United States Patent [19]
Arnold et al.

[11] Patent Number: 5,837,508
[45] Date of Patent: Nov. 17, 1998

[54] MEMBRANE-TYPE MATRIX METALLOPROTEINASE-5 GENE

[75] Inventors: Anne Romanic Arnold, Wynnewood; Anthony Joseph Arleth, Hatfield; Usman Shabon, Swarthmore, all of Pa.

[73] Assignee: Smithkline Beecham Corporation, Philadelphia, Pa.

[21] Appl. No.: 816,755

[22] Filed: Mar. 6, 1997

[51] Int. Cl.$^6$ .............................. C12N 15/57; C12N 9/64
[52] U.S. Cl. ................... 435/172.3; 435/226; 435/252.3; 536/23.2
[58] Field of Search ..................................... 435/320, 226, 435/252.3, 172.3; 536/23.2

[56] References Cited

PUBLICATIONS

EST #808618 (1997).
Puente, Xoze S., et al. "Molecular Cloning of a Novel Membrane–type Matrix Metalloproteinase from a Human Breast Carcinoma", Cancer Research 56, 944–949, Mar. 1, 1996.
Yamada, T., et al. "White matter microglia produce membrane–type matrix metalloprotease, an of gelatinase A, in human brain tissues", Acta Neuropathol (1995) 90:421–424.
Okada, A., et al. "Membrane–type matrix metalloproteinase (MT–MMP) gene is expressed in stomal cells of human colon, breast, and head and neck carcinomas", Proc. Natl. Acad. Sci. USA, vol. 92, pp. 2730–3734, Mar. 1995, Medical Sciences.
Atkinson, Susan J., et al. "Intermolecular Autolytic Cleavage Can Contribute to the Activation of Progela Progelatinase A by Cell Membranes", The Journal of Biological Chemistry, vol. 270, No. 51, Issue of Dec. 22, pp. 30479–30485, 1995.
Cao, Jian, et al. "The C–terminal Region of Membrane Type Matrix Metalloproteinase Is a functional Transmembrane Domain Required for Pro–gelatinase A Activation", The Journal of Biological Chemistry, vol. 270, No. 2, Issue of Jan. 13, pp. 801–805, (1995).
Gilles, Christine, et al. "High Level of MT–MMP Expression is Associated with Invasiveness of Cervical Cancer Cells", Int. J. Cancer: 65, 209–213 (1996).
Imai, Kazushi, et al. "Membrane–Type Matrix Metalloproteinase 1 Is a Gelantinolytic Enzyme and Is Secreted in a Complex with Tissue Inhibitor of Metalloproteinases 2$^{1}$", Cancer Research 56, 2707–2710, Jun. 15, 1996.

Nomura, Hidehiro, "Expression of Membrane–Type Matrix Metalloproteinase in Human Gastric Carcino Carcinomas", Cancer Research 55, 3263–3266, Aug. 1, 1995.
Strongin, Alex Y., "Plasma Membrane–dependent Activation of the 72–kDa Type IV Collagenase Is Prevented by Complex Formation with TIMP–2", The Journal of Biological Chemistry, vol. 268, No. 19, Issue of Jul. 5, pp. 14033–14039, (1993).
Tokuraku, Masato, et al., "Activation of the Precursor of Gelatinase A/72 kDa Type IV Collagenase/MMP–2 In Lung Carcinomas Correlates with the Expression of Membrane–Type Matrix Metalloproteinase (MT–MMP) and With Lymph Node Metastasis", Int. J. Cancer (Pred. Oncol.): 64, 335–359 (1995).
Will, Horst, et al., "The Soluble Catalytic Domain of Membrane Type 1 Matrix Metalloproteinase Cleaves the Propeptide of Progelatinase A and Initiates autoproteolytic Activation", The Journal of Biological Chemistry, vol. 271, No. 29, Issue of Jul. 19, pp. 17119–17123, 1996.
Yamamoto, Masaaki, et al. "Differential Expression of Membrane–Type matrix Metalloproteinase and Its Correlation with Gelatinase A Activation in human Malignant Brain Tumors in Vivo and in Vitro", Cancer Research 56, 384–392, Jan. 15, 1996.
Takino, Takahisa, "Identification of the Second Membrane––type Matrix Metalloproteinase (MT–mmp–2) Gene from a Human Placenta cDNA Library", The Journal of Biological Chemistry, vol. 270, No. 39, Issue of Sep. 29, pp. 23013–23020, (1995).
Will, Horst, et al., "cDNA sequence and mRNA tissue distribution of a novel human matrix metallopote metalloproteinase with a potential transmembrane segment", Eur. J. Biochem. 231, 602–608 (1995).
Sato, Hiroshi, et al., "A matrix metalloproteinase expressed on the surface of invasive tumor cells", Nature, vol. 370, Jul. 7, 61–64.

Primary Examiner—Charles L. Patterson, Jr.
Attorney, Agent, or Firm—Paul F. Prestia; Elizabeth J. Hecht; William T. King

[57] ABSTRACT

HCE3P83 polypeptides and polynucleotides and methods for producing such polypeptides by recombinant techniques are disclosed. Also disclosed are methods for utilizing HCE3P83 polypeptides and polynucleotides in the design of protocols for the treatment of Alzheimer's Disease, stroke, cancer, inflammation, arhritis, musculoskeletal disease, heart disease and kidney disease, among others, and diagnostic assays for such conditions.

19 Claims, 8 Drawing Sheets

FIG. 1

```
         10                      30                        50
GAATTCGGCTTCCGATGGTGAGTGGATCCTGCGGACGGGATGATGAAAGCATGGGTGAGG
         70                      90                       110
GGAGAAGACCCTAAACAGCTGTCTTTGTAGTCCCCGCCCACCTGGCCGGGATGCCAGCA
        130                     150                       170
ACAAGGCCACCTGCAGTCTGCCCCTGCCCCTTCCTCCCCTCAGTGGCTTTGAAGGCAGGTGT
        190                     210                       230
CCTTGAAGCTAAGCTCTGCTGGCTGCAGGTAAAACCACAGGTGGGGAGTTCTCTGAGAC
        250                     270                       290
CTAGGAGCTGGGGTGTACGGAGACCCTGCCCGGGCCGCTGAATTCTAGGTCTTGGATA
        310                     330                       350
AACTGAAAGCTTAGCGTGAACGTGGTATCACCATTGATATCTCCTTGTGAAATTTGAGA
        370                     390                       410
CCAGCAAGTACTATGTGACTATCATGGATGCCCCAGGACGATCTCCAGGGCATCCCGAAG
                                                          470
ATCTATGGACCCCCAGCCGAGCCTCTGGAGCCTACAAGGCCACTCCCTACACTCCCCGTC
        430
         M  P  Q  D  D  L  Q  G  I  P  K
 I  Y  G  P  P  A  E  P  L  E  P  T  R  P  L  P  T  L  P  V
```

FIG. 1A

```
       490                  510                    530
CGCAGGATCCACTCACCATCGGAGAGGAAACACGAGCGCCAGCCCAGCCCCCTCGGCCG
 R   R   I   H   S   P   S   E   R   K   H   E   R   Q   P   P   R   P   P   P
       550                  570                    590
CCCTCGGGGACCGGCCATCCACCAGGCACCAAACCCAACATCTGTGACGGCAACTTC
 P   S   G   D   R   P   S   T   P   G   T   K   P   N   I   C   D   G   N   F
       610                  630                    650
AACACAGTGGCCCTCTTCCGGGGCGAGATGTTTGTCTTTAAGGATCGCTGGTTCTGGCGT
 N   T   V   A   L   F   R   G   E   M   F   V   F   K   D   R   W   F   W   R
       670                  690                    710
CTGCGCAATAACCGAGTGCAGGAGGCTACCCCATGCAGATCGAGCAGTTCTGGAAGGGC
 L   R   N   N   R   V   Q   E   G   Y   P   M   Q   I   E   Q   F   W   K   G
       730                  750                    770
CTGCCTGCCCGCATCGACGCAGCCTATGAAAGGCCGATGGGAGATTTGTCTTCTTCAAA
 L   P   A   R   I   D   A   A   Y   E   R   A   D   G   R   F   V   F   F   K
       790                  810                    830
GGTGACAAGTATTGGGTGTGTTTAAGGAGGTGACGGTGGAGCCTGGGTACCCCCACAGCCTG
 G   D   K   Y   W   V   F   K   E   V   T   V   E   P   G   Y   P   H   S   L
       850                  870                    890
GGGGAGCTGGGCAGCTGTTTGCCCCGTGAAGGCATTGACACAGCTCTGCGCTGGGAACCT
 G   E   L   G   S   C   L   P   R   E   G   I   D   T   A   L   R   W   E   P
```

FIG. 1B

```
                                                      950
910           930
GTGGGCAAGACCTACTTTTTCAAAGGCGAGCGGTACTGGCGCTACAGCGAGGAGCGGCGG
 V  G  K  T  Y  F  F  F  K  G  E  R  Y  W  R  Y  S  E  E  R  R
              970                           1010
GCCACGGACCCCTGGCTACCCTAAGCCCATCACCGTGTGGAAGGGCATCCCACAGGCTCCC
 A  T  D  P  G  Y  P  K  P  I  T  V  W  K  G  I  P  Q  A  P
             1030                          1070
CAAGGAGCCTTCATCAGCAAGGAAGGATATTACACCTATTTCTACAAGGGCCGGGACTAC
 Q  G  A  F  I  S  K  E  G  Y  Y  T  Y  F  F  Y  K  G  R  D  Y
             1090                          1130
TGGAAGTTTGACAACCAGAAACTGAGCGTGGAGCCAGGCTACCCGCGCAACATCCTGCGT
 W  K  F  D  N  Q  K  L  S  V  E  P  G  Y  P  R  N  I  L  R
             1150                          1190
GACTGGGATGGGCTGCAACCAGAAGGAGGTGGAGCGGAAGGAGCGGCGGCTGCCCCAG
 D  W  D  G  C  N  Q  K  E  V  E  R  R  K  E  R  R  L  P  Q
             1210                          1250
GACGACGTGGACATCATGGTGACCATCAACGATGTGCCGGGCTCCGTGAACGCCGTGGCC
 D  D  V  D  I  M  V  T  I  N  D  V  P  G  S  V  N  A  V  A
```

FIG. 1C

```
              1270                      1290                      1310
GTGGTCATCCCCTGCATCCTGTCCCTCTGTCATCCTGGTCCTGGTGTCTACACCATCTTCCAG
 V   V   I   P   C   I   L   S   L   C   I   L   V   L   V   Y   T   I   F   Q
              1330                      1350                      1370
TTCAAGAACAAGACAAGGCCCCTCAGCCTGTCACCTACTATAAGGCGGCCAGTCCAGGAATG
 F   K   N   K   T   R   P   S   A   C   H   L   L   *
              1390                      1410                      1430
GGTGTGAGCAGCCCAGAGCCCTCTCTATCCACTTGGTCTGGCCAGCCCCAGGCCCTTCCTCA
              1450                      1470                      1490
CCAGGGTCTGAGGGGCAGCTCTGGCCAGTGCTCACCCAGGCCAGGCCCAGGCCCTAGGCTGG
              1510                      1530                      1550
GGTCGTACAGCTGAAGTGTGGGTGCATTGGCCTAGGCTGAGCGTGGGGCAGGGAATTAT
              1570                      1590                      1610
GGGGGGCTGTGCCCCAGGGGTGTCTGGCACCCAGGCTGCCAGCCTTCTGTCCTGGGCAA
              1630                      1650                      1670
ACTACTCCCTACTTAAGGAATAGGCCAGGCTCCATCCGGAGGCAGGACCATGCCAGGA
              1690                      1710                      1730
GGAGCCCCTGTGGTCACGGCATCCTGTGGTGTCCATGAGGTACCACAGCTCCACTCCTGG
              1750                      1770                      1790
CTGGAACCCAGCACCCTCTGTGGGAAGCCAGCACTAGCTCTCATCCCCCATCCGGGAGAT
```

FIG. 1D

```
        1810        1830        1850
ACCACCAGTCCTGGTCCCCTTTGCCAACACCTGCTGGTCATATGTCCCCTACCCNNAC
        1870        1890        1910
CCCACTGTCCTCCAGNGCTACAGGACCCCTGCTTNTGACACAGTGAGCAACAAGCCTGGG
        1930        1950        1970
TTTCCCTGCTGGCAGACGGCAGATCCCTCAGGNAACCTGCTCCACTTGTCAGGGTCTCTT
        1990        2010        2030
CGGAGACCCAGGATTTAGGGTCACATGCTGCAGGCAGGGCTNTGGNCNAGCTGGGTCTTA
        2050        2070        2090
CAAGGACCCAGCNTGTCANATCGTGANTATTTAAATGTNCTGTTAATNATTGTCCCATTT
        2110        2130        2150
TGCAAAGGCTGCTTTGAGGCTTTAGGTGAACTAGAGGTGACTGTCTTGGTGATGAGGCCAG
        2170        2190        2210
CATAGCGGCCCTCCCCCAGGCGACAAGGACCAAGGTGCTGCTAAGGCCACTCTAGCGCCC
        2230        2250        2270
AGACACCCAGTAGCTGAGCTCTGCTCCTATGGCTACAGAGCTGGGGCAGAAGCTGACCC
        2290        2310        2330
CATTTCTGGAGGAAGATCCGAGTTTGTGACCGTCCCTCCACTCCCCTATTGTCACTGTC
        2350        2370        2390
CCCAGCTTTGCTCCAGTCTGTCACTTGCAGCCTGGAGCTCAGCCTCACCAGTTAGGTGAG
```

FIG. 1E

```
2410                                                    2430                                                    2450
GCAGGAGATGGCTGCAGGGCCAACACTGGCAGAGCCTGGGGAGTCCTTCGGAAGGGACC
        2470                                                    2490                                                    2510
AGGGCGTCTGAAGTGCTCAGTGCCCCCACTACTCTGAGGCCGACTCCAGCTACTCTGAGG
        2530                                                    2550                                                    2570
CCGACTCAATCTCTCGGCTGGAAGCAGTGTTTTCCCAGAGCTTGGCCCTTGCTGACCTCG
        2590                                                    2610                                                    2630
CTCACTGGGCCCATCTTCCCACACTGCTCTTAGAAGGACACCCCTACCGGTAGCAGCCCC
        2650                                                    2670                                                    2690
AAGCTGAGGGGGCTCCCCTTTTTGACCTTCACTGGCCCGCCCTTCACTGTCTCCAGCAGGA
        2710                                                    2730                                                    2750
GTTCCTAGGGCTTGGCCCTGCCTTGCTCCACAGTACGGCGGAGGCAGCCCTGCTTGTCACT
        2770                                                    2790                                                    2810
GAGGAGCCCTAGACAAGGCCAATGGGTTCATCAATGCCCACTGGCTCTCTGCCAAAGCCA
        2830                                                    2850                                                    2870
AAAAGGTGTCAGGCCAGTCTCCCGGACCCTGTGGTCTCTGGGATTGGGGTCGGCTTACCCT
        2890                                                    2910                                                    2930
GAGCCTGCATGGGCCTTGCCCCGGACCCTGTGGTCTCTGGGATGCCACCCCTGCTCACT
        2950                                                    2970                                                    2990
GTAGCACAGACAGGGACTCCCTGCTGCCCTGGGGAGCTGTCTTAAGCAAAATCTCTTGTTC
```

FIG. 1F

```
3010                                                    3030                                                    3050
CCAGAGGTTGCCCATGTGTTGGTTCCGTTGTTGTTCCCTGTTCATCATCCTTGTTTTTCTT
          3070                                                    3090                                                    3110
CATTTTGGCCAAGGGAGGGTTCTTGGGACAGGCAGGGAACAATTGCGAGATATTAGTGA
          3130                                                    3150                                                    3170
TTCATAGGTTTGTACAGTTTTTTATACTTTGCAAAGCACTTTATTAGCTCACACCTGTCC
          3190                                                    3210                                                    3230
ACTCACATGAAACTCGTGTTAGGCCCTGGGAGGCGAACGGTAACTCTCACCGTGCCCTCA
          3250                                                    3270                                                    3290
GATGAAGCACAGAGAGGTTGTACTTGCCCGGGCCATCCAGTGGGCTGGCTGGGTCTTGT
          3310                                                    3330                                                    3350
GTCCCCATCTGTGGACCCCCTCTAGGGTCTGAGATGAGAGAAGTGTCTCCTGTATCCA
          3370                                                    3390                                                    3410
CCTCTTCCTGGCCTCCCTTCCCCAACTTCCTGTCCCGTCCCACTCCTCCTCAGGTTGGTGC
          3430                                                    3450                                                    3470
TCTCACTTCTTGAAAGCTCTAGGCACCCCCGCCCTCCCGCCAGGCTCCCCATTGGCTCCTG
          3490                                                    3510                                                    3530
GCAGCCCAGCTGAGAATGAACAGGAGATGGAGGCAGCCCAGGCTGCAGAGGTGAGGG
          3550                                                    3570                                                    3590
ATGTGGGGCCAGGCCCAGAGAGGCTCAGCCTAGAGAGCTTCCAATCTCAGATTCTCCTGCC
```

FIG. 1G

```
3610                3630                     3650
TGTGGTCATCTGTTTGTCCATCACCCCAGGACAGAGGGCAGACAGAGGGGCAAAGCACTGGG
     3670                3690                     3710
GGCCCCAGAGCCTAGCTTCCCCCTCAGCCTGGGGACATCACAGCATTTCAGTGTCAGTCA
     3730                3750                     3770
CATTTAAACTGATCAGCCTTTGTATAATGTTTTTAAATCATTTCTAAATAAAACAGA
     3790
AATACAAAAAAAAAAAAAAAAAAAAA
```

MEMBRANE-TYPE MATRIX METALLOPROTEINASE-5 GENE

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to Membrane-Type Matrix Metalloproteinase family, hereinafter referred to as HCE3P83. The invention also relates to inhibiting or activating the action of such polynucleotides and polypeptides.

BACKGROUND OF THE INVENTION

Membrane-Type Matrix Metalloproteinases (MT-MMPs) are a new family of transmembrane matrix metalloproteinases. At present, there are four MT-MMPs published in the literature (Sato, H. et al., Nature 370:61–65, 1994; Will, H. and Hinzmann, B. Eur. J. Biochem. 231:602–608, 1995; Talino, T. et al., J. Biol. Chem. 270:23013–23020; Puente, X. S. et al., Cancer Res. 56:944–949, 1996). MT-MMPs function as both a receptor and as an activator for certain MMPs and serve to localize extracellular matrix proteolysis at the pericellular region. MT-MMPs have been shown to play a role in metastasis and have been identified in numerous carcinomas. An MT-MMP has also been demonstrated to be involved in Alzheimer's Disease where it has been found in white matter microglia (Yamada, T. et al., Acta Neuropathol. 90: 421–424, 1995). MT-MMPs may also play a role in the infiltration of inflammatory cells. By Northern Array Grid Analysis, MT-MMP-5 expression was detected in cerebellum and kidney. A multiple tissue Northern blot was also probed for MT-MMP-5, which indicated the presence of MT-MMP-5 in brain, kidney and pancreas. This indicates that these Membrane-Type Matrix Metalloproteinases have an established, proven history as therapeutic targets. Clearly, there is a need for identification and characterization of further members of the Membrane-Type Matrix Metalloproteinase family which can play a role in preventing, ameliorating or correcting dysfunctions or diseases, including, but not limited to, Alzheimer's Disease, stroke, cancer, inflammation, arthritis, musculoskeletal disease, heart disease and kidney disease.

SUMMARY OF THE INVENTION

In one aspect, the invention relates to HCE3P83 polypeptides and recombinant materials and methods for their production. Another aspect of the invention relates to methods for using such HCE3P83 polypeptides and polynucleotides. Such uses include the treatment of Alzheimer's Disease, stroke, cancer, inflammation, arthritis, musculoskeletal disease, heart disease and kidney disease, among others. In still another aspect, the invention relates to methods to identify agonists and antagonists using the materials provided by the invention, and treating conditions associated with HCE3P83 imbalance with the identified compounds. Yet another aspect of the invention relates to diagnostic assays for detecting diseases associated with inappropriate HCE3P83 activity or levels.

BRIEF DESCRIPTION OF THE DRAWINGS

FIG. 1 shows the nucleotide and deduced amino acid sequence of human HCE3P83 (SEQ ID NOS: 1 and 2).

DESCRIPTION OF THE INVENTION

Definitions

The following definitions are provided to facilitate understanding of certain terms used frequently herein.

"HCE3P83" refers generally to a polypeptide having the amino acid sequence set forth in SEQ ID NO:2 or an allelic variant thereof.

"HCE3P83 activity or HCE3P83 polypeptide activity" or "biological activity of the HCE3P83 or HCE3P83 polypeptide" refers to the metabolic or physiologic function of said HCE3P83 including similar activities or improved activities or these activities with decreased undesirable side-effects. Also included are antigenic and immunogenic activities of said HCE3P83.

"HCE3P83 polypeptides" refers to polypeptides with amino acid sequences sufficiently similar to HCE3P83 sequences, preferably exhibiting at least one biological activity of the HCE3P83.

"HCE3P83 gene" refers to a polynucleotide having the nucleotide sequence set forth in SEQ ID NO: 1 or allelic variants thereof and/or their complements.

"HCE3P83 polynucleotides" refers to polynucleotides containing a nucleotide sequence which encodes a HCE3P83 polypeptide or fragment thereof, or a nucleotide sequence which has at least 65% identity to a nucleotide sequence encoding the polypeptide of SEQ ID NO:2 or the corresponding fragment thereof, or a nucleotide sequence which has sufficient identity to a nucleotide sequence contained in SEQ ID NO: 1 to hybridize under conditions useable for amplification or for use as a probe or marker.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS - STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTITRANSLATIONAL COVALENT MODIFI-CATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIO-COMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., SIAM *J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., SIAM *J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(l):387), BLASTP, BLASTN, and FASTA (Atschul, S. F. et al., *J Molec Biol* (1990) 215:403).

Polypeptides of the Invention

The HCE3P83 polypeptides of the present invention include the polypeptide of SEQ ID NO:2 (in particular, the mature polypeptide) as well as HCE3P83 polypeptides and which have at least 59% identity to the polypeptide of SEQ ID NO:2 or the relevant portion and more preferably at least 80% identity, and still more preferably at least 90% identity, and even still more preferably at least 95% identity to SEQ ID NO: 2. HCE3P83 of the invention is structurally related to other proteins of the Membrane-Type Matrix Metalloproteinase family, as shown by the results of sequencing the cDNA encoding human HCE3P83. The cDNA sequence contains an open reading frame encoding a protein of 324 amino acids with a deduced molecular weight of 37763 kDa.. HCE3P83 of FIG. 1 (SEQ ID NO:2) has about 59% identity (using FASTA) in 324 amino acid residues with Membrane-Type Matrix Metalloproteinase-3 (Takino, T. et al., J. Biol. Chem. 270:23013–23020, 1995). Other known MT-MMPs include: Membrane-Type Matrix Metalloproteinase-2 (Will, H. and Hinzmann, B.. Eur. J. Biochem. 231:602–608, 1995); Membrane-Type Matrix Metalloproteinase-1 (Sato, H. et al., Nature 370:61–65, 1994); Membrane-Type Matrix Metalloproteinase-4 (Puente, X. S. et al., Cancer Res. 56:944–949, 1996). The HCE3P83 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Biologically active fragments of the HCE3P83 polypeptides are also included in the invention. A fragment is a polypeptide having an amino acid sequence that entirely is the same as part, but not all, of the amino acid sequence of the aforementioned HCE3P83 polypeptides. As with HCE3P83 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of HCE3P83 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HCE3P83 polypeptides, except for deletion of a continuous series of residues that includes the amino termiinus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate HCE3P83 activity, including those with a similar activity or an improved activity, or with a decreased undesirable activity. Also included are those that are antigenic or immunogenic in an animal, especially in a human.

Thus, the polypeptides of the invention include polypeptides having an amino acid sequence at least 59% identical to that of SEQ ID NO:2 or fragments thereof with at least 59% identity to the corresponding fragment of SEQ ID NO:2. Preferably, all of these polypeptides retain the biological activity of the HCE3P83, including antigenic activity. Included in this group are variants of the defined sequence and fragments. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The HCE3P83 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to isolated polynucleotides which encode the HCE3P83 polypeptides and polynucleotides closely related thereto.

HCE3P83 gene of FIG. 1 (SEQ ID NO: 1) has about 65% identity (using FASTA) in 995 nucleotide residues with Membrane-Type Matrix Metalloproteinase-3 (Takino, T., J. Biol. Chem. 270:23013–23020, 1995). Other related polynucleotide sequences are: Membrane-Type Matrix Metalloproteinase-2 (Will, H. and Hinzmann,B.. Eur. J. Biochem. 231:602–608, 1995); Membrane-Type Matrix Metalloproteinase-1 (Sato, H. et al., Nature 370:61–65, 1994); and Membrane-Type Matrix Metalloproteinase-4 (Puente, X. S. et al., Cancer Res. 56:944–949, 1996).

One polynucleotide of the present invention encoding HCE3P83 may be obtained using standard cloning and screening, from a cDNA library derived from mRNA in cells of human cerebellum using the expressed sequence tag (EST) analysis (Adams, M. D., et al. *Science* (1991) 252:1651–1656; Adams, M. D. et al., *Nature*, (1992) 355:632–634; Adams, M.D., et al., *Nature* (1995) 377 Supp:3–174). Polynucleotides of the invention can also be obtained from natural sources such as genomic DNA libraries or can be synthesized using well known and commercially available techniques.

Thus, the nucleotide sequence encoding HCE3P83 polypeptides may be identical over its entire length to the coding sequence in FIG. 1 (SEQ ID NO: 1), or may be a degenerate form of this nucleotide sequence encoding the polypeptide of SEQ ID NO:2, or may be highly identical to a nucleotide sequence that encodes the polypeptide of SEQ ID NO:2. Preferably, the polynucleotides of the invention contain a nucleotide sequence that is highly identical, at least 65% identical, with a nucleotide sequence encoding a HCE3P83 polypeptide, or at least 65% identical with the encoding nucleotide sequence set forth in FIG. 1 (SEQ ID NO: 1), or at least 65% identical to a nucleotide sequence encoding the polypeptide of SEQ ID NO:2.

When the polynucleotides of the invention are used for the recombinant production of HCE3P83 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Among particularly preferred embodiments of the invention are polynucleotides encoding HCE3P83 polypeptides having the amino acid sequence of set out in FIG. 1 (SEQ ID NO:2) and variants thereof.

Further preferred embodiments are polynucleotides encoding HCE3P83 variants that have the amino acid sequence of the HCE3P83 polypeptide of FIG. 1 (SEQ ID NO:2) in which several, 5–10, 1–5, 1–3, 1–2 or 1 amino acid residues are substituted, deleted or added, in any combination.

Further preferred embodiments of the invention are polynucleotides that are at least 65% identical over their entire length to a polynucleotide encoding the HCE3P83 polypeptide having the amino acid sequence set out in FIG. 1 (SEQ ID NO:2), and polynucleotides which are complementary to such polynucleotides. In this regard, polynucleotides at least 80% identical over their entire length to the same are particularly preferred, and those with at least 90% are especially preferred. Furthermore, those with at least 97% are highly preferred and those with at least 98–99% are most highly preferred, with at least 99% being the most preferred.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are sufficiently identical to a nucleotide sequence contained in SEQ ID NO:1, may be used as hybridization probes for cDNA and genomic DNA, to isolate full-length cDNAs and genomic clones encoding HCE3P83 polypeptide and to isolate cDNA and genomic clones of other genes that have a high sequence similarity to the HCE3P83 gene. Such hybridization techniques are known to those of skill in the art. Typically these nucleotide sequences are 70% identical, preferably 80% identical, more preferably 90% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING: A LABORATORY MANUAL*, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HCE3P83 polypeptide is to be expressed for use in screening assays, generally, it is preferred that the polypeptide be produced at the surface of the cell. In this event, the cells may be harvested prior to use in the screening assay. If HCE3P83 polypeptide is secreted into the medium, the medium can be recovered in order to recover and purify the polypeptide; if produced intracellularly, the cells must first be lysed before the polypeptide is recovered.

HCE3P83 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of HCE3P83 polynucleotides for use as diagnostic reagents. Detection of a mutated form of HCE3P83 gene associated with a dysfunction will provide a diagnostic tool that can add to or define a diagnosis of a disease or susceptibility to a disease which results from under-expression, over-expression or altered expression of HCE3P83. Individuals carrying mutations in the HCE3P83 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HCE3P83 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and SI protection or the chemical cleavage method. See Cotton et al., *Proc Natl Acad Sci USA* (1985) 85: 4397–4401. In another embodiment, an array of oligonucleotide probes comprising HCE3P83 nucleotide sequences of fragments therof can be constructed to conduct efficient screeing of e.g., genetic mutations. Array technology methods are well known and have general applicability and can be used to address a variety of questions in molecular genetics, including gene expression, genetic linkage, and genetic variability. See, e.g., M. Cheel, et. al. Science, vol. 274, pp 610–613 (1996).

The diagnostic assays offer a process for diagnosing or determining a susceptibility to Alzheimer's DiseaseAlzheimer's Disease, stroke, cancer, inflammation, arthritis, musculoskeletal disease, heart disease and kidney disease through detection of mutation in the HCE3P83 gene by the methods described.

In addition, Alzheimer's DiseaseAlzheimer's Disease, stroke, cancer, inflammation, arthritis, musculoskeletal disease, heart disease and kidney disease, can be diagnosed by methods comprising determining from a sample derived from a subject an abnormally decreased or increased level of HCE3P83 polypeptide or HCE3P83 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an HCE3P83 polypeptide, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the HCE3P83 polypeptides. The term "immunospecific" means that the antibodies have substantial greater affinity for the polypeptides of the invention than their affinity for other related polypeptides in the prior art.

Antibodies generated against the HCE3P83 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against HCE3P83 polypeptides may also be employed to treat Alzheimer's DiseaseAlzheimer's Disease, stroke, cancer, inflammation, arthritis, musculoskeletal disease, heart disease and kidney disease, among others.

Vaccines

Another aspect of the invention relates to a method for inducing an immunological response in a mammal which comprises inoculating the mammal with HCE3P83 polypeptide, or a fragment thereof, adequate to produce antibody and/or T cell immune response to protect said animal from Alzheimer's Disease, stroke, cancer, inflammation, arthritis, musculoskeletal disease, heart disease and kidney disease, among others. Yet another aspect of the invention relates to a method of inducing immunological response in a mammal which comprises, delivering HCE3P83 gene via a vector directing expression of HCE3P83 polypeptide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a HCE3P83 polypeptide wherein the composition comprises a HCE3P83 polypeptide or HCE3P83 gene. The vaccine formulation may further comprise a suitable carrier. Since HCE3P83 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The HCE3P83 polypeptide of the present invention may be employed in a screening process for compounds which activate (agonists) or inhibit activation of (antagonists, or otherwise called inhibitors) the HCE3P83 polypeptide of the present invention. Thus, polypeptides of the invention may also be used to assess identify agonist or antagonists from, for example, cells, cell-free preparations, chemical libraries, and natural product mixtures. These agonists or antagonists may be natural substrates, ligands, receptors, etc., as the case may be, of the polypeptide of the present invention; or may be structural or functional mimetics of the polypeptide of the present invention. See Coligan et at, *Current Protocols in Immunology* 1(2):Chapter 5 (1991).

HCE3P83 proteins are ubiquitous in the mammalian host and are responsible for many biological functions, including many pathologies. Accordingly, it is desirous to find compounds and drugs which stimulate HCE3P83 polypeptide on the one hand and which can inhibit the function of HCE3P83 polypeptide on the other hand. In general, agonists are employed for therapeutic and prophylactic purposes for such conditions as Alzheimer's Disease, stroke, cancer, inflammation, arthritis, musculoskeletal disease, heart disease and kidney disease. Antagonists may be employed for a variety of therapeutic and prophylactic purposes for such conditions as Alzheimer's Disease, stroke, cancer, inflammation, arthritis, musculoskeletal disease, heart disease and kidney disease.

In general, such screening procedures may involve producing appropriate cells which express the HCE3P83 polypeptide of the present invention on the surface thereof. Such cells include cells from mammals, yeast, Drosophila or *E. coli*. Cells expressing the HCE3P83 polypeptide (or cell membrane containing the expressed polypeptide) are then contacted with a test compound to observe binding, or stimulation or inhibition of a functional response.

Cells expressing the HCE3P83 polypeptide (or cell membrane containing the expressed polypeptide) will be amenable to the development of a high-throughput screen for the purpose of identifying potential therapeutic inhibitors. Further, HCE3P83 expressed in a "null" cell (a cell which does not express HCE3P83 endogenously) can be used to characterize the physiological and pathophysiological properties of the expressed polypeptide.

The assays may simply test binding of a candidate compound wherein adherence to the cells bearing the HCE3P83 polypeptide is detected by means of a label directly or indirectly associated with the candidate compound or in an assay involving competition with a labeled competitor. Further, these assays may test whether the candidate compound results in a signal generated by activation of the HCE3P83 polypeptide, using detection systems appropriate to the cells bearing the HCE3P83 polypeptide at their surfaces. Inhibitors of activation are generally assayed in the presence of a known agonist and the effect on activation by the agonist by the presence of the candidate compound is observed. Standard methods for conducting such screening assays are well understood in the art.

Examples of potential HCE3P83 polypeptide antagonists include antibodies or, in some cases, oligonucleotides or proteins which are closely related to the ligands, substrates, receptors, etc., as the case may be, of the HCE3P83 polypeptide, e.g., a fragment of the ligands, substrates, receptors, or small molecules which bind to the polypetide of the present invention but do not elicit a response, so that the activity of the polypeptide is prevented.

Prophylactic and Therapeutic Methods

This invention provides methods of treating an abnormal conditions related to both an excess of and insufficient amounts of HCE3P83 polypeptide activity.

If the activity of HCE3P83 polypeptide is in excess, several approaches are available. One approach comprises administering to a subject an inhibitor compound (antagonist) as hereinabove described along with a pharmaceutically acceptable carrier in an amount effective to inhibit activation by blocking binding of ligands to the HCE3P83 polypeptide, or by inhibiting a second signal, and thereby alleviating the abnormal condition.

In another approach, soluble forms of HCE3P83 polypeptides still capable of binding the ligand in competition with endogenous HCE3P83 polypeptide may be administered. Typical embodiments of such competitors comprise fragments of the HCE3P83 polypeptide.

In still another approach, expression of the gene encoding endogenous HCE3P83 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of HCE3P83 and its activity, several approaches are also available. One approach comprises administering to a subject a therapeutically effective amount of a compound which activates HCE3P83 polypeptide, i.e., an agonist as described above, in combination with a pharmaceutically acceptable carrier, to thereby alleviate the abnormal condition. Alternatively, gene therapy may be employed to effect the endogenous production of HCE3P83 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of HCE3P83 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide er vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1: Cloning Method

A partial clone (ATG 844, HGS EST #808618) was initially identified through targeted searches of a database comprising a collection of sequenced human ESTs (see Adams, M. D., supra) using sequence data of the transmembrane domains of the four known MT-MMPs. This partial clone (2.7 kb, which encodes 97 residues at the C-termiinal region) showed significant homology to MT-MMP-3. To get the full-length clone, First Human Skeletal muscle cDNA (Marathon Ready, Clontech, Palo Alto, Calif.) was used with nested antisense primers to amplify the missing 5' region. The PCR conditions were as follows: 94° C. for 1 min; 5 cycles: 94° C. 30 sec; 72° C. 4 min; 5 cycles: 94° C. 30 sec; 70° C. 4 min; 25 cycles: 94° C. 30 sec; 68° C. 4 min. An 800 bp product was obtained, this fragment was subcloned in to PCR 2.1 vector (Invitrogen, San Diego, Calif.) and sequenced. This fragment extended the above partial clone an additional 240 residues. New reverse Marathon oligos were designed based on new sequence and used with Human full brain cDNA (Marathon Ready, Palo Alto, Calif.) in PCR reaction. The PCR conditions were identical to the first reaction. A 400 bp product was obtained which was subcloned and sequenced, this extended above sequence further, and the entire coding region was obtained. To confirm the above results, similar fragments were obtained by using the Human Cerebellum cDNA (Marathon Ready) as a template with aforementioned PCR primers and conditions. The final full length cDNA is 975 bp and encodes for 324 amino acids. To get the fall length gene, two sets of nested primers were designed the sequence of the first set was:

(5' sense 5'-GGATAA ACTGAAAGCTTAGCGTGA ACGTGG-3' (SEQ ID NO: 3) and 3' antisense primer: 5'-CAGCTGTACGACCCCAGCCTAGGG-3') (SEQ ID NO: 4) and the sequence of second set was:

(5' sense CGAGGTGAA TTCGCCACCATGCCCCAG-GACGATCTC -3' (SEQ ID NO: 5) and 3' antisense primer: 5'- CTAGAACTAGITIATAGTAGGTGACA-GGCT-3') (SEQ ID NO: 6). EcoRI and SpeI restriction sites were designed in the second set of primers for subcloning purposes. Human full brain Gene Trapper Library (Gibco, BRL Bethesda, Md.) was used as a template with above primers. The final product from this PCR was a 1 kb fragment as expected.

What is claimed is:

1. An isolated polynucleotide comprising a nucleotide sequence that has at least 80% identity over its entire length to a nucleotide sequence coding the polypeptide of SEQ ID NO:2 said identity being calculated using FASTA with the sequences aligned to obtain the highest order match between the sequences.

2. The polynucleotide of claim 1 which is DNA or RNA.

3. The polynucleotide of claim 1 wherein said nucleotide sequence is at least 80% identical to that contained in SEQ ID NO: 1 said identity being calculated using FASTA with the sequences aligned to obtain the highest order match between the sequences.

4. The polynucleotide of claim 3 wherein said nucleotide sequence is contained in SEQ ID NO:1.

5. The polynucleotide of claim 1 wherein said encoding nucleotide sequence encodes the polypeptide of SEQ ID NO:2.

6. The isolated polynucleotide of claim 1 wherein said nucleotide sequence has at least 90% identity to a polynucleotide encoding the polypeptide of SEQ ID NO:2 said identity being over the entire region coding for SEQ ID NO:2 and being calculated using FASTA with the sequences aligned to obtain the highest order match between the sequences.

7. The isolated polynucleotide of claim 1 wherein said nucleotide sequence has at least 95% identity to a polynucleotide encoding the polypeptide of SEQ ID NO:2 said identity being over the entire region coding for SEQ ID NO:2 and being calculated using FASTA with the sequences aligned to obtain the highest order match between the sequences.

8. The isolated polynucleotide of claim 1 wherein said nucleotide sequence has at least 80% identity to the entire coding region contained in SEQ ID NO:1 said identity being calculated using FASTA with the sequences aligned to obtain the highest order match between the sequences.

9. The isolated polynucleotide of claim 1 wherein said nucleotide sequence has at least 90% identity to the entire coding region contained in SEQ ID NO:1 said identity being calculated using FASTA with the sequences aligned to obtain the highest order match between the sequences.

10. The isolated polynucleotide of claim 1 wherein said nucleotide sequence has at least 95% identity to the entire coding region contained in SEQ ID NO: 1 said identity being calculated using FASTA with the sequences aligned to obtain the highest order match between the sequences.

11. The isolated polynucleotide of claim 1 wherein said nucleotide sequence is the entire length of the RNA transcript of SEQ ID NO:1.

12. The isolated polynucleotide of claim 1 wherein said nucleotide sequence is the coding region of the RNA transcript of SEQ ID NO:1.

13. An expression system comprising a DNA or RNA molecule wherein said expression system is capable of producing a HCED3P83 polypeptide having at least 80% identity over its entire length with the polypeptide of SEQ ID NO:2 when said expression system is present in a compatible host cell said identity being calculated using FASTA with the sequences aligned to obtain the highest order match between the sequences.

14. A host cell comprising the expression system of claim 7.

15. A process for producing a HCE3P83 polypeptide comprising culturing a host of claim 14 under conditions sufficient for the production of said polypeptide.

16. The process of claim 15 wherein said polypeptide is expressed at the surface of said cell.

17. The process of claim 15 which further includes recovering the polypeptide from the culture.

18. A process for producing a cell which produces a HCE3P83 polypeptide comprising transforming or transfecting a host cell with the expression system of claim 13 such that the host cell, under appropriate culture conditions, produces a HCE3P83 polypeptide.

19. A polynucleotide sequence which is complementary to any of the isolated polynucleotides in any one of claims 1, 5 and 7–12.

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 3807 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GAATTCGGCT  TCCGATGGTG  AGTGGATCCT  GCGGACGGGA  TGATGAAAGC  ATGGGTGAGG      60

GGAGAAGACC  CTAAACAGCT  GTCTTTGTTA  GTCCCCGCCC  ACCTGGCCGG  GATGCCAGCA     120

ACAAGGCCAC  CTGCAGTCTG  CCCTGCCCTT  CCTCCCCTCA  GTGGCTTTGA  AGGCAGGTGT     180

CCTTGAAGCT  AAGCTCTGCT  GGCTGCAGGT  AAAACCACAG  GTGGGGGAGT  TCTCTGAGAC     240
```

| | | | | | |
|---|---|---|---|---|---|
| CTAGGAGCTG | GGGTGTACGG | AGACCTGCCC | GGGCGGCCGC | TGAATTCTAG | GTCTTGGATA | 300
| AACTGAAAGC | TTAGCGTGAA | CGTGGTATCA | CCATTGATAT | CTCCTTGTGG | AAATTTGAGA | 360
| CCAGCAAGTA | CTATGTGACT | ATCATGGATG | CCCCAGGACG | ATCTCCAGGG | CATCCCGAAG | 420
| ATCTATGGAC | CCCCAGCCGA | GCCTCTGGAG | CCTACAAGGC | CACTCCCTAC | ACTCCCCGTC | 480
| CGCAGGATCC | ACTCACCATC | GGAGAGGAAA | CACGAGCGCC | AGCCCAGGCC | CCTCGGCCG | 540
| CCCTCGGGGG | ACCGGCCATC | CACACCAGGC | ACCAAACCCA | ACATCTGTGA | CGGCAACTTC | 600
| AACACAGTGG | CCCTCTTCCG | GGGCGAGATG | TTTGTCTTTA | AGGATCGCTG | GTTCTGGCGT | 660
| CTGCGCAATA | ACCGAGTGCA | GGAGGGCTAC | CCCATGCAGA | TCGAGCAGTT | CTGGAAGGGC | 720
| CTGCCTGCCC | GCATCGACGC | AGCCTATGAA | AGGGCCGATG | GGAGATTTGT | CTTCTTCAAA | 780
| GGTGACAAGT | ATTGGGTGTT | TAAGGAGGTG | ACGGTGGAGC | CTGGGTACCC | CCACAGCCTG | 840
| GGGGAGCTGG | GCAGCTGTTT | GCCCCGTGAA | GGCATTGACA | CAGCTCTGCG | CTGGGAACCT | 900
| GTGGGCAAGA | CCTACTTTTT | CAAAGGCGAG | CGGTACTGGC | GCTACAGCGA | GGAGCGGCGG | 960
| GCCACGGACC | CTGGCTACCC | TAAGCCCATC | ACCGTGTGGA | AGGGCATCCC | ACAGGCTCCC | 1020
| CAAGGAGCCT | TCATCAGCAA | GGAAGGATAT | TACACCTATT | CTACAAGGG | CCGGGACTAC | 1080
| TGGAAGTTTG | ACAACCAGAA | ACTGAGCGTG | GAGCCAGGCT | ACCCGCGCAA | CATCCTGCGT | 1140
| GACTGGATGG | GCTGCAACCA | GAAGGAGGTG | GAGCGGCGGA | AGGAGCGGCG | GCTGCCCCAG | 1200
| GACGACGTGG | ACATCATGGT | GACCATCAAC | GATGTGCCGG | GCTCCGTGAA | CGCCGTGGCC | 1260
| GTGGTCATCC | CCTGCATCCT | GTCCCTCTGC | ATCCTGGTGC | TGGTCTACAC | CATCTTCCAG | 1320
| TTCAAGAACA | AGACAAGGCC | CTCAGCCTGT | CACCTACTAT | AAGCGGCCAG | TCCAGGAATG | 1380
| GGTGTGAGCA | GCCCAGAGCC | CTCTCTATCC | ACTTGGTCTG | GCCAGCCAGG | CCCTTCCTCA | 1440
| CCAGGGTCTG | AGGGGCAGCT | CTGGCCAGTG | CTCACCAGGG | CCAGCAGGGC | CCTAGGCTGG | 1500
| GGTCGTACAG | CTGAAGTGGT | GGGTGCATTG | GCCTAGGCTG | AGCGTGGGGC | AGGGAATTAT | 1560
| GGGGGCTGTG | CCCCAGGGTG | GGTGTCTGGC | ACCCAGCTGC | CAGCCTTCTG | TCCTGGGCAA | 1620
| ACTACTCCCT | ACTTAAGGGA | ATAGGCCAGG | CTCCATCCGG | AGGCAGGGAC | CATGCCAGGA | 1680
| GGAGCCCCTG | TGGTCACGGC | ATCCTGTGGT | GTCCATGAGG | TACCACAGCT | CCACTCCTGG | 1740
| CTGGAACCCA | GCACCCTCTG | TGGGAAGCCA | GCACTAGCTC | TCATCCCCCA | TCCGGGAGAT | 1800
| ACCACCAGTC | CTGGTCCCCT | TTTGCCAACA | CCTGCTGGTC | ATATGTCCCC | CTACCCNNAC | 1860
| CCCACTGTCC | TCCAGNGCTA | CAGGACCCCT | GCTTNTGACA | CAGTGAGCAA | CAAGCCTGGG | 1920
| TTTCCCTGCT | GGCAGACGGC | AGATCCCTCA | GGNAACCTGC | TCCACTTGTC | AGGGTCTCTT | 1980
| CGGAGACCCA | GGATTTAGGG | TCACATGCTG | CAGGCAGGGC | TNTGGNCNAG | CTGGGTCTTA | 2040
| CAAGGACCCA | GCNTGTCANA | TCGTGANTAT | TTAAATGTNC | TGTTAATNAT | TGTCCCATTT | 2100
| TGCAAAGGCT | GCTTGAGGCT | TTAGGTGAAC | TAGAGGTGAC | TGTCTTGGTG | ATGAGGCCAG | 2160
| CATAGCGGCC | CTCCCCCAGG | CGACAAGGAC | CAAGGTGCTG | CTAAGGCCAC | TCTAGCGCCC | 2220
| AGACACCCCA | GTAGCTGAGC | TCTGCTCCTA | TGGCTACAGA | GCTGGGGCAG | AAGCTGACCC | 2280
| CATTTCTGGA | GGAAGATCCG | AGTTTGTGAC | CGTCCTCCAC | TCCCCTCTAT | TGTCACTGTC | 2340
| CCCAGCTTTG | CTCCAGTCTG | TCACTTGCAG | CCTGGAGCTC | AGCCTCACCA | GTTAGGTGAG | 2400
| GCAGGAGATG | GCTGCAGGGC | CAACACTGGC | AGAGCTGGG | GAGTCCTTCG | GAAGGGACC | 2460
| AGGGCGTCTG | AAGTGCTCAG | TGCCCCCACT | ACTCTGAGGC | CGACTCCAGC | TACTCTGAGG | 2520
| CCGACTCAAT | CTCTCGGCTG | GAAGCAGTGT | TTTCCCAGAG | CTTGGCCCTT | GCTGACCTCG | 2580
| CTCACTGGGC | CCATCTTCCC | ACACTGCTCT | TAGAAGGACA | CCCCTACCGG | TAGCAGCCCC | 2640

-continued

| | | | | | |
|---|---|---|---|---|---|
| AAGCTGAGGG | GGCTCCCTTT | TTGACCTTCA | CTGGCCCGCC | CTTCACTGTC | TCCAGCAGGA | 2700
| GTTCCTAGGG | CTTGGCCTGC | CTTGCTCCAC | AGTACGGCGG | AGGCAGCCCT | GCTTGTCACT | 2760
| GAGGAGCCCT | AGACAAGGCC | AATGGGTTCA | TCAATGCCCA | CTGGCTCTCT | GCCAAAGCCA | 2820
| AAAAGGTGTC | AGGCAGTCTC | CAGCGTGCTG | GCCGGGTCTC | GGATGCCACC | CCTGCTCACT | 2880
| GAGCCTGCAT | GGGCCTTGCC | CCGGACCCTG | TGGTCTCTGG | GATTGGGGTC | GGCTTACCCT | 2940
| GTAGCACAGA | CAGGGACTCC | TGCTGCCCTG | GGGAGCTGTC | TTAAGCAAAA | TCTCTTGTTC | 3000
| CCAGAGGTTG | CCCATGTTGG | TTCCGTTGTT | GTTCCCTGTT | CATCATCCTT | GTTTTTCTT | 3060
| CATTTTGGCC | AAGGGAGGGT | TCTTGGGACA | GGCAGGGAAC | AATTGCGGAG | ATATTAGTGA | 3120
| TTCATAGGTT | TGTACAGTTT | TTTATACTTT | GCAAAGCACT | TTATTAGCTC | ACACCTGTCC | 3180
| ACTCACATGA | AACTCGTGTT | AGGCCCTGGG | AGGCGAACGG | TAACTCTCAC | CGTGCCCTCA | 3240
| GATGAAGCAC | AGAGAGGTTG | TTACTTGCCC | GGGCCATCCA | GTGGGCTGGC | TGGGTCTTGT | 3300
| GTCCCCATCT | GTGGACCCCT | CTAGGGTCTG | AGATGAGATG | AGAAGTGTCT | CCTGTATCCA | 3360
| CCTCTTCCTG | GCCTCCCTTC | CCCCAACTTC | CTGGTCCCTG | TCCACTCCTC | AGGTTGGTGC | 3420
| TCTCACTTCT | TGAAAGCTCT | AGGCACCCCC | GCCTCCCGCC | AGGCTCCCCA | TTGGCTCCTG | 3480
| GCAGCCCAGC | TGAGAATGAA | CAGGAGATGG | AGGCAGCAGC | CCAGGCTGCA | GAGGTGAGGG | 3540
| ATGTGGGGGC | CAGGCCCAGA | GGGCTCAGCC | TAGAGGCTTC | CAATCTCAGA | TTCTCCTGCC | 3600
| TGTGGTCATC | TGTTTGTCCA | TCACCCCAGG | ACAGGGCAGA | CAGAGGGGCA | AAGCACTGGG | 3660
| GGCCCCAGAG | CCTAGCTTCC | CCTCAGCCTG | GGGGACATCA | CAGCATTTCA | GTGTCAGTCA | 3720
| CATTTTAAAC | TGATCAGCCT | TTGTATAATG | TTTTTAAAT | CATTTCTAAA | ATAAAACAGA | 3780
| AATACAAAAA | AAAAAAAAA | AAAAAA | | | | 3807

(2) INFORMATION FOR SEQ ID NO:2:

(i) SEQUENCE CHARACTERISTICS:
        (A) LENGTH: 324 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met  Pro  Gln  Asp  Asp  Leu  Gln  Gly  Ile  Pro  Lys  Ile  Tyr  Gly  Pro  Pro
 1                   5                  10                  15

Ala  Glu  Pro  Leu  Glu  Pro  Thr  Arg  Pro  Leu  Pro  Thr  Leu  Pro  Val  Arg
                20                  25                  30

Arg  Ile  His  Ser  Pro  Ser  Glu  Arg  Lys  His  Glu  Arg  Gln  Pro  Arg  Pro
                35                  40                  45

Pro  Arg  Pro  Pro  Ser  Gly  Asp  Arg  Pro  Ser  Thr  Pro  Gly  Thr  Lys  Pro
     50                  55                  60

Asn  Ile  Cys  Asp  Gly  Asn  Phe  Asn  Thr  Val  Ala  Leu  Phe  Arg  Gly  Glu
 65                  70                  75                  80

Met  Phe  Val  Phe  Lys  Asp  Arg  Trp  Phe  Trp  Arg  Leu  Arg  Asn  Asn  Arg
                85                  90                  95

Val  Gln  Glu  Gly  Tyr  Pro  Met  Gln  Ile  Glu  Gln  Phe  Trp  Lys  Gly  Leu
                100                 105                 110

Pro  Ala  Arg  Ile  Asp  Ala  Ala  Tyr  Glu  Arg  Ala  Asp  Gly  Arg  Phe  Val
               115                 120                 125

Phe  Phe  Lys  Gly  Asp  Lys  Tyr  Trp  Val  Phe  Lys  Glu  Val  Thr  Val  Glu
          130                 135                 140
```

-continued

| | | | | | | | | | | | | | | |
|---|---|---|---|---|---|---|---|---|---|---|---|---|---|---|
| Pro | Gly | Tyr | Pro | His | Ser | Leu | Gly | Glu | Leu | Gly | Ser | Cys | Leu | Pro | Arg |
| 145 | | | | | 150 | | | | | 155 | | | | | 160 |

| Glu | Gly | Ile | Asp | Thr | Ala | Leu | Arg | Trp | Glu | Pro | Val | Gly | Lys | Thr | Tyr |
|---|---|---|---|---|---|---|---|---|---|---|---|---|---|---|---|
| | | | | 165 | | | | | 170 | | | | | 175 | |

| Phe | Phe | Lys | Gly | Glu | Arg | Tyr | Trp | Arg | Tyr | Ser | Glu | Glu | Arg | Arg | Ala |
|---|---|---|---|---|---|---|---|---|---|---|---|---|---|---|---|
| | | | 180 | | | | | 185 | | | | | 190 | | |

| Thr | Asp | Pro | Gly | Tyr | Pro | Lys | Pro | Ile | Thr | Val | Trp | Lys | Gly | Ile | Pro |
|---|---|---|---|---|---|---|---|---|---|---|---|---|---|---|---|
| | | 195 | | | | | 200 | | | | | 205 | | | |

| Gln | Ala | Pro | Gln | Gly | Ala | Phe | Ile | Ser | Lys | Glu | Gly | Tyr | Tyr | Thr | Tyr |
|---|---|---|---|---|---|---|---|---|---|---|---|---|---|---|---|
| | 210 | | | | | | 215 | | | | | 220 | | | |

| Phe | Tyr | Lys | Gly | Arg | Asp | Tyr | Trp | Lys | Phe | Asp | Asn | Gln | Lys | Leu | Ser |
|---|---|---|---|---|---|---|---|---|---|---|---|---|---|---|---|
| 225 | | | | | 230 | | | | | 235 | | | | | 240 |

| Val | Glu | Pro | Gly | Tyr | Pro | Arg | Asn | Ile | Leu | Arg | Asp | Trp | Met | Gly | Cys |
|---|---|---|---|---|---|---|---|---|---|---|---|---|---|---|---|
| | | | | 245 | | | | | 250 | | | | | 255 | |

| Asn | Gln | Lys | Glu | Val | Glu | Arg | Arg | Lys | Glu | Arg | Arg | Leu | Pro | Gln | Asp |
|---|---|---|---|---|---|---|---|---|---|---|---|---|---|---|---|
| | | | 260 | | | | | 265 | | | | | 270 | | |

| Asp | Val | Asp | Ile | Met | Val | Thr | Ile | Asn | Asp | Val | Pro | Gly | Ser | Val | Asn |
|---|---|---|---|---|---|---|---|---|---|---|---|---|---|---|---|
| | | 275 | | | | | 280 | | | | | 285 | | | |

| Ala | Val | Ala | Val | Val | Ile | Pro | Cys | Ile | Leu | Ser | Leu | Cys | Ile | Leu | Val |
|---|---|---|---|---|---|---|---|---|---|---|---|---|---|---|---|
| | 290 | | | | | 295 | | | | | 300 | | | | |

| Leu | Val | Tyr | Thr | Ile | Phe | Gln | Phe | Lys | Asn | Lys | Thr | Arg | Pro | Ser | Ala |
|---|---|---|---|---|---|---|---|---|---|---|---|---|---|---|---|
| 305 | | | | | 310 | | | | | 315 | | | | | 320 |

Cys His Leu Leu (2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGATAAACTG AAAGCTTAGC GTGAACGTGG        30

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CAGCTGTACG ACCCCAGCCT AGGG        24

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CGAGGTGAAT TCGCCACCAT GCCCCAGGAC GATCTC        36

(2) INFORMATION FOR SEQ ID NO:6:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:6:

CTAGAACTAG TTTATAGTAG GTGACAGGCT   30